United States Patent
Carey

(10) Patent No.: US 12,246,050 B2
(45) Date of Patent: Mar. 11, 2025

(54) POST EXTRACTION PURIFICATION OF TERPENES

(71) Applicant: Vapor Oil Technology LLC, Jackson, MI (US)

(72) Inventor: Chad Arthur Carey, Pheonix, AZ (US)

(73) Assignee: Vapor Oil Technology LLC, Jackson, MI (US)

( * ) Notice: Subject to any disclaimer, the term of this patent is extended or adjusted under 35 U.S.C. 154(b) by 374 days.

(21) Appl. No.: 17/990,991

(22) Filed: Nov. 21, 2022

(65) Prior Publication Data

US 2023/0083465 A1   Mar. 16, 2023

Related U.S. Application Data

(63) Continuation-in-part of application No. 17/960,682, filed on Oct. 5, 2022, now Pat. No. 11,793,785.

(51) Int. Cl.
| | |
|---|---|
| *A61K 31/352* | (2006.01) |
| *A23L 33/105* | (2016.01) |
| *A61K 9/00* | (2006.01) |
| *A61K 31/015* | (2006.01) |
| *A61K 31/045* | (2006.01) |
| *A61K 36/185* | (2006.01) |
| *B01D 11/02* | (2006.01) |

(52) U.S. Cl.
CPC .......... *A61K 36/185* (2013.01); *A23L 33/105* (2016.08); *A61K 9/0053* (2013.01); *A61K 31/015* (2013.01); *A61K 31/045* (2013.01); *A61K 31/352* (2013.01); *B01D 11/0269* (2013.01); *B01D 11/0288* (2013.01); *A23V 2002/00* (2013.01); *A61K 2236/51* (2013.01); *A61K 2236/53* (2013.01)

(58) Field of Classification Search
CPC . A61K 31/352; A61K 2236/55; A23L 33/105; B01D 11/0269; B01D 11/0288
See application file for complete search history.

(56) References Cited

U.S. PATENT DOCUMENTS

| | | |
|---|---|---|
| 8,192,589 B2 | 6/2012 | Winkelaar et al. |
| 10,688,410 B2 | 6/2020 | Dimitrelos et al. |
| 10,793,498 B2 | 10/2020 | Jansen et al. |
| 10,973,255 B2 | 4/2021 | Pandolfino |
| 11,141,680 B2 | 10/2021 | Gildrien |
| 11,266,702 B2 | 3/2022 | Speier |
| 2016/0045471 A1 | 2/2016 | Stodola |
| 2018/0099236 A1 | 4/2018 | Shuja |
| 2020/0222828 A1 | 7/2020 | Rutz et al. |
| 2020/0237840 A1 | 7/2020 | Morrow |
| 2020/0239428 A1 | 7/2020 | Raber et al. |
| 2021/0251157 A1 | 8/2021 | Leo |
| 2022/0110991 A1 | 4/2022 | Backes |
| 2022/0241699 A1 * | 8/2022 | Wirtz ....................... B01D 8/00 |
| 2023/0000132 A1 | 1/2023 | Carey |
| 2023/0040806 A1 | 2/2023 | Carey |

FOREIGN PATENT DOCUMENTS

| | | |
|---|---|---|
| WO | 2021-086675 A2 | 5/2021 |
| WO | WO2022/1555741 A1 | 7/2022 |

* cited by examiner

*Primary Examiner* — Sikarl A Witherspoon
(74) *Attorney, Agent, or Firm* — Kevin H. Fortin

(57) ABSTRACT

A method of purifying cannabis derived terpenes includes first providing cannabis material having a detectable amount of tetrahydrocannabinolic acid (THCA), adding a solvent to the cannabis material, spinning the cannabis material in a centrifuge to separate crystallized THCA from a high terpene extract. Decarboxilating the THCA with heat to yield tetrahydrocannabinol. The high terpene extract is deposited into a vacuum oven to reduce pressure and volatilize terpenes from the high terpene extract. Next the terpenes are pumped into a cold trap to condense terpenes from the high terpene extract. Next, the condensed terpenes are cooled at a temperature between −50° C. and 0° C. to remove water from the condensed terpenes and yield purified terpenes. The purified terpenes are applied to an edible food product containing decarboxylated tetrahydrocannabinol. In an alternate embodiment, the tetrahydrocannabinol and the purified terpenes are combined or recombined and mixed directly into a precooked edible food product.

20 Claims, 4 Drawing Sheets

POST EXTRACTION PURIFICATION OF TERPENES

CROSS-REFERENCE TO RELATED APPLICATION

This patent application is a continuation-in-part of co-pending U.S. patent application Ser. No. 17/960,682, filed 5 Oct. 2022, the disclosure of which is incorporated herein by reference.

FIELD OF THE INVENTION

The present invention relates to efficient ways of purifying terpenes extracted from *Cannabis sativa*, and particularly to the use of a centrifuge, a vacuum oven, and cold trap in combination.

BACKGROUND OF THE INVENTION

The term "THC" usually refers to the trans-$\Delta^9$-tetrahydrocannabinol, which is a $\Delta^9$ isomer. The term "THC crystals", is often a misnomer. While THC can be formed into a glass-like sheet called shatter, or a distillate powder, it does not naturally crystallize under most conditions.

Tetrahydrocannabinolic acid "THCA" can naturally crystallize when in a concentrated solution. In ideal conditions THCA crystals naturally form. Some believe that it is easier under most circumstances to use crystallization to concentrate THCA than it is to concentrate THC.

THCA has two major isomers, THCA-A, in which the carboxylic acid group is in the 1 position, between the hydroxy group and the carbon chain, and THCA-B, in which the carboxylic acid group is in the 3 position, following the carbon chain. Both isomers, when crystallized, typically have a colorless appearance. The terms "tetrahydrocannabinolic acid", and "THCA", as used herein includes both of these isomers.

In addition to the cannabinoids described above, another aspect of processing cannabinoids involves the separation of volatile plant terpenes that accompany the cannabinoids in *Cannabis sativa* plants. This is called the "terpene mix".

Terpenes have boiling point at 1 ATM of pressure that are disparate and vary as compared to cannabinoids. Distillation boils the terpenes to separate them, but also looses some in the process. Boiling points of typical terpenes and cannabinoids can be seen from Table 1 and Table 2 below.

Boiling point temperatures of various cannabis terpenes:

TABLE 1

A-Pinene (156° C./312° F.)
Beta-Caryophyllene (119° C./246° F.)
B-Myrcene (166-168° C./330-334° F.)
Limonene (177° C./350° F.)
Linalool (198° C./388° F.)
Humulene (198° C./388° F.)

Boiling point temperatures of various cannabinoids:

TABLE 2

THCA Tetrahydrocannabinolic Acid (105° C./221° F.)
THC Tetrahydrocannabinol (157° C./314° F.)
THCV Tetrahydrocannabivarin (220° C./428° F.)
CBDA Cannabidiolic Acid (120° C./248° F.)
CBD Cannabidiol (160-180° C./320-356° F.)

TABLE 2-continued

CBC Cannabichromene (220° C./428° F.)
CBN Cannibinol (185° C./365° F.)

Some terpene purification processes, such as a rotovape, may require disconnection of vacuum to refill the rotating element, and to empty the reservoir. Releasing vacuum can loose terpenes to ambient air, which is inefficient and may change the concentrations of terpenes in the terpene mix of any terpene mixture product.

What is desired is a way to prevent losses which can change the terpene profile of any purified terpene product mixture. What is also desired is a way to prevent losses that limit terpene mixture yield.

Freeze driers have been used to separate terpenes, and do not require excessive heat. However, freeze driers rely on sublimation to separate terpenes. Sublimation is a slow process, and there can be condensation in transport lines, which must be drained. Condensation in transport lines wastes terpenes and changes terpene ratios in the terpene mix yielded by the process.

What is desired is a way to separate terpenes from a high terpene extract containing some cannabinoids. What is also desired is a way to separate terpenes from a high terpene extract that is a post process to a cold extraction of cannabinoid pre-process, so that the terpenes are preserved post removal of many or most of the cannabinoids. What is also desired is a way to separate terpenes from a high terpene extract to yield a terpene mixture product with no detectable cannabinoids, or nearly zero detectable cannabinoids. What is also desired is a purified terpene extract mixture product that mimics a terpene profile of input cannabis materials to preserve any entourage effect when adding, or re-combining, the purified terpene extract mixture to purified cannabinoids.

SUMMARY OF THE INVENTION

Edible cannabis products require decarboxylated THC, to deliver a "high" effect to a consumer. The entourage effect is achieved by combining a terpene mixture that is reflective of the ratio of terpenes in the terpene mix of particular cannabis strains.

The present invention specifically includes a method of purifying cannabis derived terpenes includes first providing cannabis material having a detectable amount of tetrahydrocannabinolic acid (THCA), adding a solvent to the cannabis material, spinning the cannabis material in a centrifuge to separate crystallized THCA from a high terpene extract. Decarboxilating the THCA with heat to yield tetrahydrocannabinol. The high terpene extract is deposited into a vacuum oven to reduce pressure and volatilize terpenes from the high terpene extract. Next the terpenes are pumped into a cold trap to condense terpenes from the high terpene extract. Next, the condensed terpenes are cooled at a temperature between −50° C. and 0° C. to remove water from the condensed terpenes and yield purified terpenes. The purified terpenes are applied to an edible food product containing decarboxylated tetrahydrocannabinol. In an alternate embodiment, the tetrahydrocannabinol and the purified terpenes are combined or recombined and mixed directly into a precooked edible food product.

It can be appreciated that applying, mixing, or otherwise including the purified terpenes to a food product fortifies the food product with volatile terpenes in their natural, unheated and unadulterated form. This yields superior aroma, and flavor. Mixing the purified terpenes with a pre-decarboxilated THC product and the food product enables an entourage effect in a way similar to consuming the original cannabis material via smoking. The user has the benefit of decarboxylated THC, and the aroma and flavor of the terpenes, without having to smoke cannabis material.

Numerous other product can include the purified terpenes, including beverages where flavor defects are sought to be avoided, vaporizable oils which are optimized for aroma and flavor, massage oils, soaps, and numerous consumer products desiring a naturally occurring aroma that mimics cannabis material. The present invention can be used to add purified terpenes to a THC distillate powder to mimic the original cannabis material in both aroma and entourage.

One key aspect of the invention is to first remove and decarboxilate THCA prior to handling terpenes from original cannabis material. This yields THC as a first product and a high terpene mixture as a second product. Both can be recombined in one aspect of the invention to yield an additive free cannabis product with decarboxilated THC and natural unprocessed and unheated terpenes. They can also be separated and used in separate channels of commerce.

Another aspect of this invention is that the purified terpenes can be added to a pre-pasteurized beverage to provide desired flavor and aroma.

Removing Most Cannabinoids Using Crystalization of THCA

The present invention includes utilizing two primary steps to yield a concentrated THC cannabis product that is purple in color without the use of dyes or additives. This THC cannabis concentrate product can be modified in various post processing steps to make shatter or distillate having aroma and flavor, without additives not found in the original cannabis material used for the process. Various consumer products can be manufactured using the post processed THC product, which typically is purple in color, having at least 90% THC content. Such consumer products may be engineered to have a desirable flavor and aroma. The form of this concentrated THC product can be a glass-like shatter product or packaged distillate, for example. More preferably the consumer products have a greater than 95% THC content.

The first step is to use a centrifuge to achieve THCA separation. Optimally this is accomplished by centrifuging rosin press filter bags of cannabis material and including a suitable solvent such as pentane or hexane. In various alternate embodiments, the filter bags are replaced with stainless steel baskets or other shape 20-30 micron filters. Preferably the filter has an average of 25 micron pore diameter size in all embodiments.

The pentane partially, or fully saturates, the cannabis material. Preferably the cannabis material is full spectrum cannabis oil having at least 60% THCA content. The filter bags have pores with an average diameter of 25 microns to retain THCA within the bags during the centrifuge process. This concentrates the THCA to over 95% purity, and often over 98% purity, yielding a first concentrated THCA product. This is a very fast an efficient way to achieve a concentrated THCA product.

The first step also yields a wash bi-product including THCA, terpenes and pentane solvent, which are recoverable using conventional processes such as high pressure liquid chromatography, ethanol distillation, or a mechanical means such as a centrifuge.

Both the first concentrated THCA product and THCA can be recovered from the wash bi-product and decarboxylated into a viscous liquid having at least 95% THC concentration.

Alternatively, the wash bi-product can be lightly purged and then introduced to other products. It is possible to extract pure terpenes from the wash bi-product, and these pure terpenes can be selectively mixed with a purple shatter product in accord with the present invention to add flavor and aroma, without degrading the integrity of the purple shatter product either in texture, hardness and color. In a preferred embodiment, the pure terpenes constitute no more than 1-2% of the shatter product.

In an alternate embodiment the wash bi-product can be introduced into a purple THC product used as vaporizable oil, packaged for use in a vaporizer cartridge, or packaged in a vaporizer cartridge. In this embodiment, the terpene level can be up to 10%. Optimally, the product packaged for and used in a vaporizer cartridge has a THC concentration between 95%-99%.

In another embodiment that is important to the invention, the wash bi-product can be cold processed into a purified terpene mixture product through the use of a pressure oven operating at vacuum pressure, and a cold trap.

The second step is to introduce the decarboxylated THC product into a wiped film evaporator, which is technically a short path evaporator that uses a thin film and a mechanical blade to speed the process of distillation/evaporation. The wiped film evaporator is primarily used to oxidize the concentrated THC product. This transforms the concentrated THC product on a continuous basis into a thin film that is wiped by a rotating blade to rapidly oxidize the concentrated THC product and thereby yield an oxidized THC product that is purple in color.

In an alternate embodiment of the product of the invention, various terpenes are mixed into the oxidized THC product to provide aroma and flavor. These various terpenes typically do not arise to more than 1-2% of the terpene-infused alternate product.

In yet another alternate embodiment, the oxidized THC product is processed again in the wiped film evaporator to achieve an above 99% purity and to assure optimal oxidation. This step may repeat.

In a variation of the step of using the centrifuge, the cannabis material is saturated by dripping pentane onto it and bagging the saturated cannabis material in a filter bag having a 25 micron pore size, a stainless steel basket having 25 micron pore sizes, or other filter. The step of centrifuging the saturated cannabis material whisks a wash bi-product from the cannabis material out of the filter bag via the 25 micron pores.

This wash bi-product is a high terpene extract (HTE) and contains some THCA along with terpenes, which are both recoverable. The present invention processes the high terpene extract to preserve the terpenes in a ratio that mimics the concentrations in the terpene mix of the original cannabis material. This yields a purified terpene mixture product that can be added to an edible cannabis product having decarboxilated THC to achieve an entourage effect without requiring additional terpene additives. The present invention also yields a plant-like aroma that mimics the original cannabis material. The benefit is that the cannabis material can be decarboxilated prior to adding to the edible product and the terpenes can be preserved, not wasted, and presented into the edible product without being regulated as a separate food additive.

The purified terpene product can also be added to THC distillate to make a concentrated THC product that smells like the original cannabis plant material. The purified terpene product can also be packaged and sold as food, beverage, cosmetic or smokable ingredients for vaporizers or smokable cannabis products.

Manufacturing Efficiency Improvement

The centrifuged THCA product is provide quickly and may immediately yield over half of the THCA available, in a pure form. In parallel, the high terpene extract (HTE) byproduct can be conventionally processed to yield THCA. The HTE byproduct also includes terpenes and residual pentane that can be processed conventionally. Thus both methods are utilized in parallel. The amount of material conventionally processed is halved to achieve manufacturing efficiency.

Recovery of THCA from the HTE entails removing or evaporating the pentane and re-dissolving the dry HTE in butane. This enables the THA-A to crystallize in the butane rich environment.

In another embodiment, the recovery of THCA from the HTE entails placing the HTE into a sealed container such as a jar, and spinning the container of the HTE in the centrifuge. Removing the jar enables formation of pure THCA crystals over time to improve yield of the THCA product.

Simply stated, a number of ways are used to process the wash bi-product to re-crystallize and to recover THCA that was not initially recovered in the filter bag. An advantage of stems from the fact that that the bi-product wash can be speedily processed via conventional and mechanical means while the wiped film evaporator runs. This manufacturing efficiency utilizes parallel processes at the same time to more rapidly product concentrated cannabis products. It is estimated that the parallel processing the THCA using a centrifuge and the HTE processing at the same time cuts product time in half, or stated differently increases production capacity by 2×, with a greater efficiency in terms of yield. More terpenes are preserved when separated and purged at lower temps such as the mechanical processing (centrifuge) enables. Mechanical processing at lower temperatures (below the decarboxylation temperature of THCA) also maintains the integrity of the THCA so that it can be most efficiently separated or extracted.

In one embodiment the step of re-capturing using butane is at room temperature and after saturation allows the butane to evaporate in a vented room as the evaporative process cools the mixture allowing the THCA to form crystals. This process can take less than 24 hours. The HTE byproduct yields 10%-90% THCA in the form of white crystals and requires a minimum of mechanical equipment, space and energy. These THCA crystals can then be fully decarboxilated into THC.

The THC is then oxidized by heating in a wiped film evaporator to achieve a purified and purple colored product. The HTE byproduct can also be further processed to extract terpenes that can be added back to the purified and purple colored product to add flavor and aroma.

Decarboxylation Timing

Decarboxylation of the THCA can occur prior to processing in the wiped film evaporator, can occur while in the wiped film evaporator, or after the wiped film evaporator processes the concentrated cannabis material.

Heat hastens decarboxylation and also oxidation. 95%+ THC can be kept as a viscous liquid having a very light yellow color. This viscous liquid is spread thin in wiped film evaporator to oxidize and pull non-THC components out, yielding an oxidized, decarboxilated and highly purified THC having at least a 90% THC concentration, and preferably 98-99% THC concentration. Natural oxidation occurs to the highly purified THC due to thin sheet geometry, which maximizes surface area exposed to ambient oxygen. This oxidation turns the highly purified THC purple in color naturally without dies or additives. In one embodiment oxygen is introduced into the wiped film evaporator to more rapidly oxidize the THC. In this embodiment, less heat is required. In an alternate embodiment a reactive oxygen species is introduced such as superoxide.

In a post process, terpenes are added to the highly purified THC that is purple in color to yield shatter having a greater than 95% THC concentration. The purple color is retained. Simply stated, removing terpenes destabilizes THC to enable it to oxidize and turn purple, then terpenes can be added back to provide aroma and flavor. Grinding the shatter makes a purple colored crystallized distillate product that can be packaged in a jar.

In another post process, the crystallized purple distillate product is used to make beverages, gummies, candies, and other edible product. Since the distillate product is highly concentrated, this post process may include adding anthocyanins to optimize color. The anthocyanins can be produced from powdered fruit, for example, by saturating with pentane in a filter bag and centrifuging to yield a purified anthocyanin. Blueberry powder, for example, can be used to yield a blue anthocyanin food grade dye that can be added to post process products to enhance color. In an alternate embodiment, beet root can be processed in a manner similar to anthocyanin to yield betalains that can be used as a post process food grade natural dye.

DETAILED DESCRIPTION

The present invention relies upon a centrifuge to rotate cannabis material in nylon rosin filter bags having a 25 micron average pore size. A C1D2 model centrifuge such as sold by C1D1 Labs having a 100 gallon capacity, or other capacity, can be used in accordance with the present invention.

In one embodiment the cannabis material is extracted cannabis oil having a THCA content and secondary material including terpenes. The centrifuge separates the secondary materials from the tetrahydrocannabinolic acid from to yield a concentrated cannabis material having at least 95% tetrahydrocannabinolic acid (THCA), and preferably 98-99% THCA. This THCA is decarboxylated and transferred into a wiped film evaporator for oxidation and, in various embodiments, additional decarboxylation.

Figure 1:
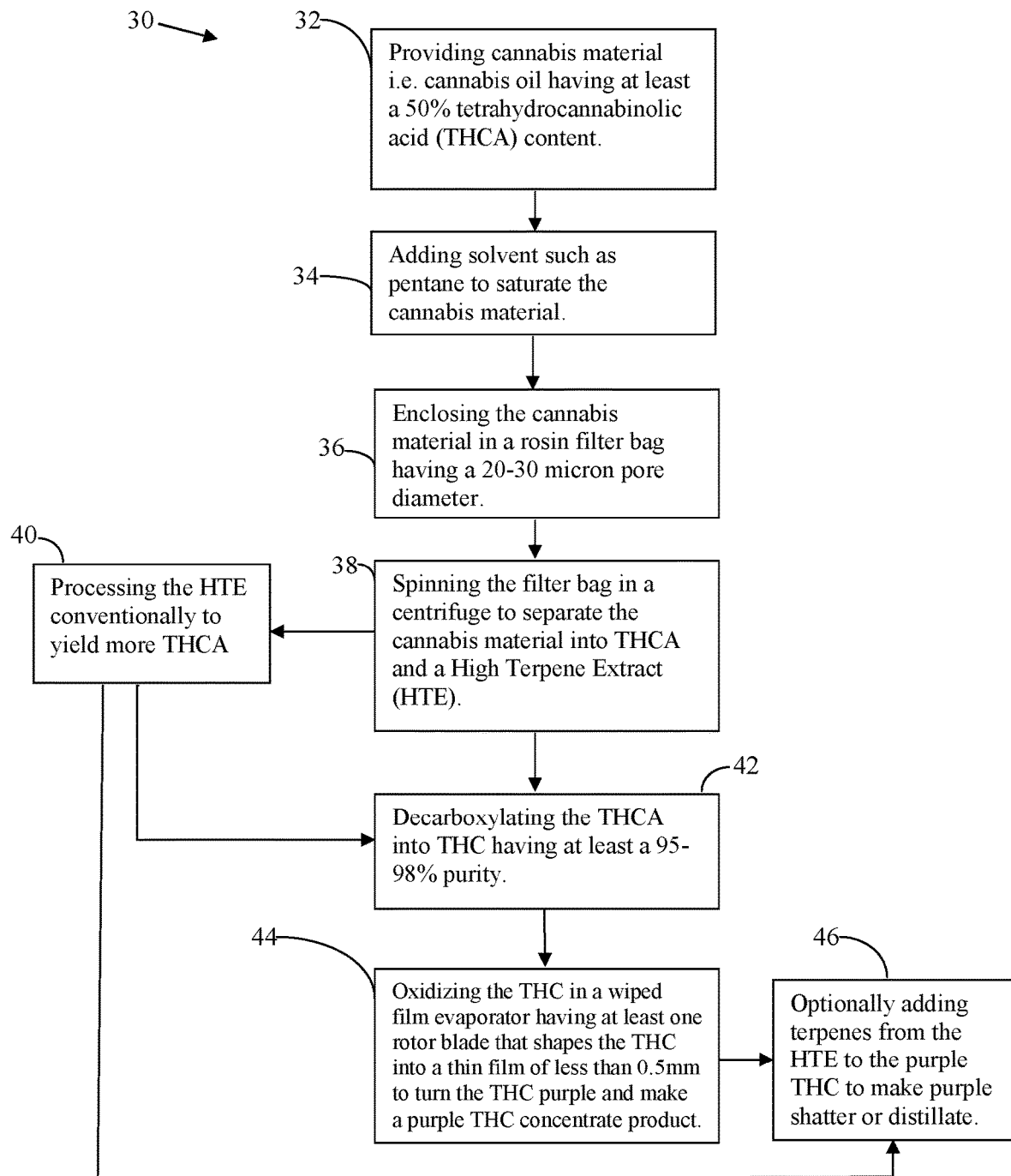
FIG. 1 is a flow chart for using a wiped film evaporator to purify and oxidize THC into a purple color.

FIG. 1 is a flow chart describing a method 30 of efficiently manufacturing a concentrated and decarboxilated THC product that is purple in color, and has at least 98% THC content. This concentrated product can be mixed with cannabis terpenes to add flavor and aroma. Various consumer products can be made with this concentrated product including shatter and distillate that is packaged in a jar.

The method 30 includes the step 32 of providing cannabis material. In one embodiment, the cannabis material can be full spectrum cannabis oil, typically having at least a 50% THCA content. It can have any amount of THCA, but using oil with at least 50%, and preferably at least 60% is more efficient than using cannabis material having a lesser concentration of THCA.

The step 34 follows and solvent is added to the cannabis material to separate the THCA. The solvent can be selected from the group consisting of acetic acid, other acid, ethanol, other alcohols, hydrocarbons, pentane, hexane, butane or other solvent. Preferably pentane is used because it is relatively non-toxic, readily available, rapidly effective, and relatively inexpensive. The pentane partially saturates, or fully saturates, the cannabis material. Preferably the pentane is dripped onto the cannabis material.

The step 36 encloses the cannabis material in a rosin filter bag having a 20-30 micron pore diameter, or alternatively a stainless steel basket having a similar pore diameter. This step 36 can come prior to the step 34 of adding solvent, or afterwards. Preferably, the rosin filter bag has an average pore diameter of 25 microns+/−1 micron. The filter bags are typically made from nylon, or other polymer capable of resisting solvent and heat of at least 300° F. These rosin filter bags are used because they are widely available for rosin press users, and are inexpensive. The present invention includes the discovery that these rosin press bags are suitable for use in a centrifuge, and while not super efficient, can greatly increase efficiency of select manufacturing processes that produce purified and oxidized THC products.

The filter bag is spun in the step 38 in a centrifuge to separate the cannabis material into pure (<95%) THCA and a High Terpene Extract (HTE). Preferably the THCA is purified to greater than 98%.

The step 40 processes the HTE conventionally to yield more THCA. The HTE includes THCA, terpenes, and solvent (pentane) so removing of the solvent can enable isolation and separation of this additional THCA, and the particular terpenes. High Pressure Liquid Chromatography (HPLC), vacuum distillation in a rotating vaporizer, or processes, for example, can remove and isolate the particular terpenes and the THCA.

In one embodiment, the step 40 is modified to be novel and unconventional. Pentane from the HTE is removed. The HTE is saturated with butane. The butane and HTE mixture can be shelved for 24 hours to allow the butane to evaporate at standard temperature and pressure, leaving THCA crystals and terpenes. Both the THCA and terpenes can be used in accord with the present invention is post process steps. The THCA can be mixed with the THCA removed from the rosin filter bag and both can be decarboxilated as per step 42 into THC having at least 95-98% concentration, or greater concentration, and next fed to a wiped film evaporator, or short path distillation device, or similar device, to enable oxidation of the THC to purify the THC and turn the THC purple.

The step 44 oxidizes the THC in a wiped film evaporator having at least one rotor blade that shapes the THC into a thin film of less than 0.5 mm to turn the THC purple and make a purple THC concentrate product. While a thin film is used to process the THC, rolled films and other methods may be applicable to generate the purple color and optimally concentrate the THC to above 98% purity.

The step 46 optionally adds terpenes from the HTE to the purple THC to make a purple distillate or shatter product having desired aroma and flavor, and a THC purity of between 95% and 98%.

All purities and concentrations expressed herein are on a weight to weight (w:w) basis. The filter basket or filter bag can include any shape or suitable material having an approximately 25 micron pore diameter for use in the centrifuge. While the present invention is described by way of example only, the detailed scope of the invention is set forth in the appended claims.

Figure 2:
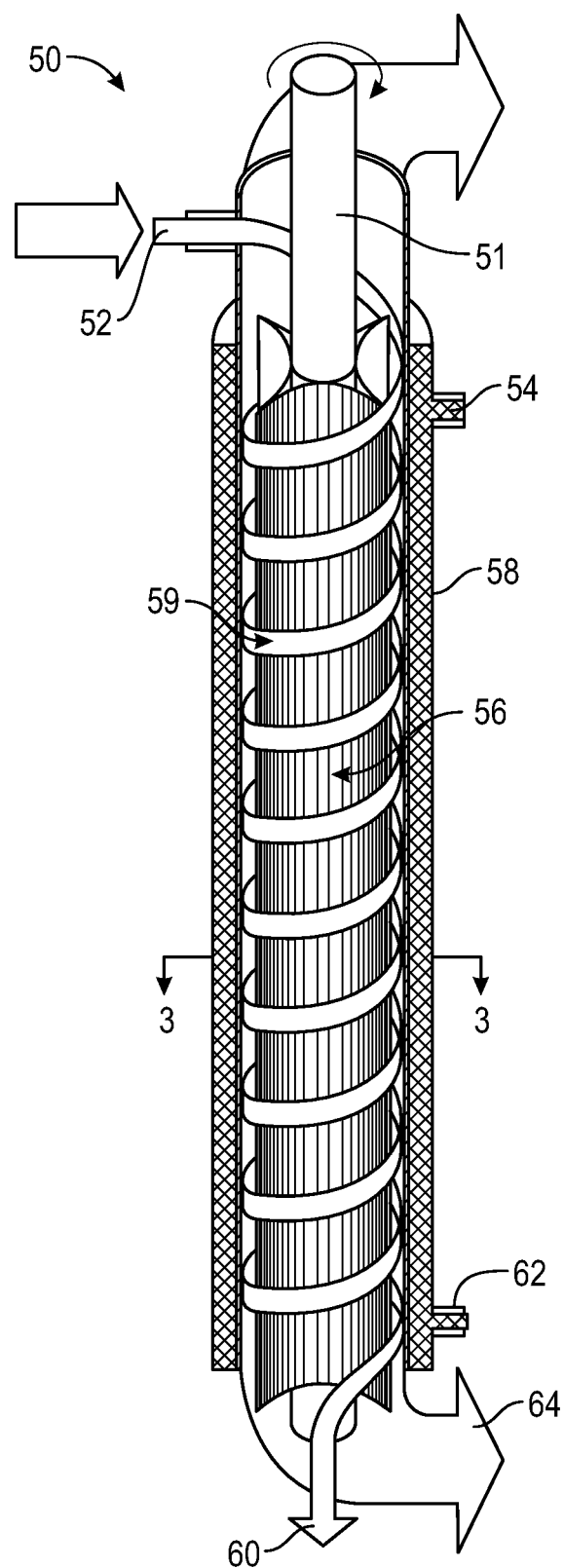
FIG. 2 is an example of the wiped film evaporator.

FIG. 2 is a Wiped Film Evaporator (WFE) generally designated with the reference numeral 50. The WFE includes a rotatable shaft 51, a feed port 52, a heating input port 54 a rotor 56 connected with the shaft 51 that rotates a plurality of aligned auger blades aligned with an axis of the shaft 51, a shell 58, a product exhaust port 60, a heating fluid output port 62. In variations of the WFE 50, the WFE includes a vacuum port, residue port, cooling water ports and a vapor exhaust port 64.

The wiped film evaporator (WFE) 50 is a piece of commercially available equipment normally used for concentration, distilling, stripping, dehydration and deodorization of products which are heat sensitive or viscous. The equipment can handle a very wide range of feed compositions ranging from 1% to over 98% THC concentrations.

In accord with the present invention, the WFE 50 has several advantages and newly discovered unique functions for thin film oxidation of THC to yield a purple THC product. The operation is continuous. Continuous contact wipers or blades 56 produce and renew the thin film, whose thickness effects any rate of oxidation. Such an operation improves product yield while enabling oxidation of the cannabis material having at least 95% THC, and preferably greater than 98% THC.

The operation process in the WFE 50 is simple but yet effective. Feed material i.e. THC is introduced at the top of the unit an passes in a helical direction 59 to form a thin film that spreads on the shell 58 inner surface in response to the shaft 51 rotation. Specially designed wipers or blades 56 wipe the feed material thus creating and renewing the film. This thin film enables an efficient heat transfer and oxidation. The non-THC components having a relatively lower boiling point evaporate and pass through an entrainment separator. These non-THC components are removed through the vapor exhaust port 64. In one embodiment oxygen is fed through the feed port 52 along with THC to enhance the oxidation of the thin film.

The THC is transferred out through the distillate port in a concentration of at least 98%. Importantly the WFE uses a rotating bladed system to wipe a layer of film with each pass to enable oxidation of the THCA that is exposed to ambient oxygen at controlled temperatures and pressures. The THCA is further concentrated in one embodiment to nearly 99% purity and at this purity the THCA readily changes color to purple under appropriate environmental conditions at which the WFE device is controlled to operate.

Figure 3:
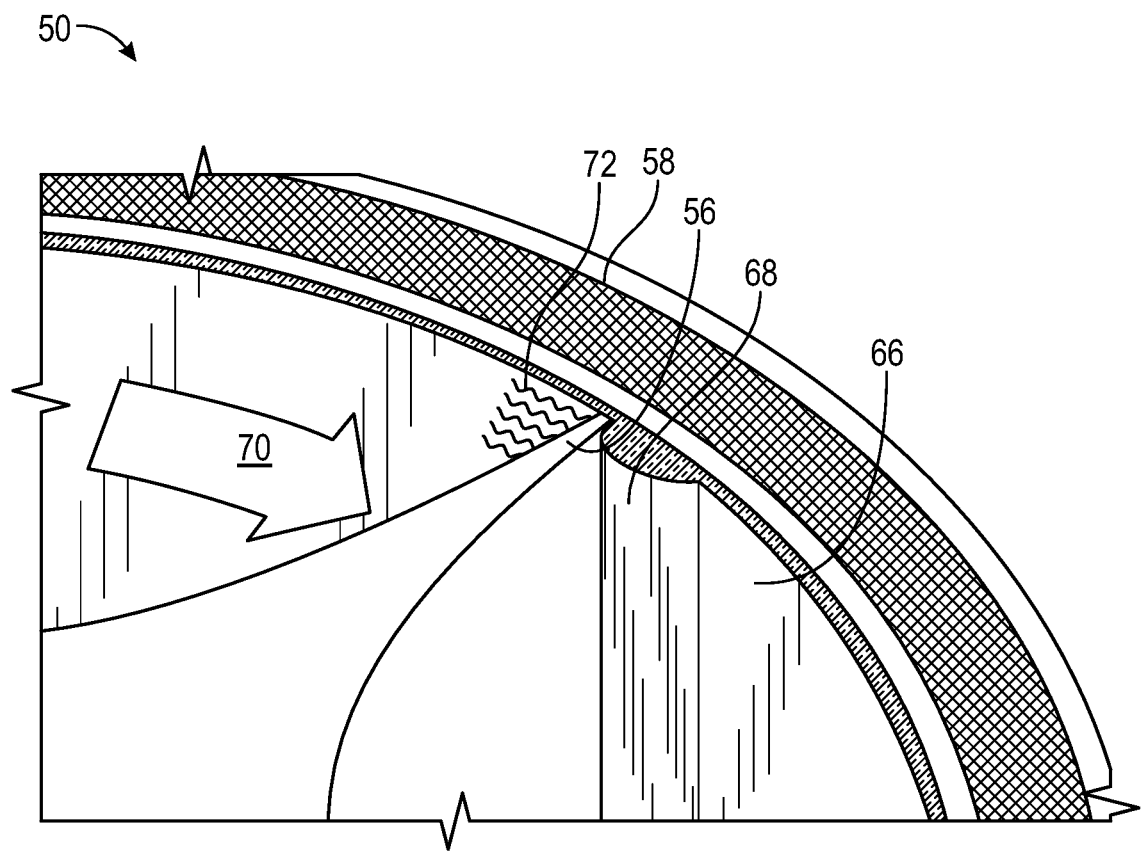
FIG. 3 is a partial sectional view of the rotor blade of the wiped film evaporator of FIG. 2 as seen along the line 3-3.

FIG. 3 shows the operation of the WFE 50. It includes the shell 58 having a cylindrical interior coated with THC 66. The WFE 50 includes a rotatable blade 56 that skims the THC 66 under suitable temperature and pressure to create a bow wave 68, and yield a thin film 72 behind the blade 56 opposing the bow wave 68. The wiped thin film material is sent via the outlet 60 of the WFE 50 in FIG. 2 as super concentrated cannabis material having a THC concentration of at least 95%, and preferably at least 98%.

While a commercially available WFE is shown by way of example, many devices can achieve optimal distillation of the cannabis material having THC in high concentrations such as above 98% to oxidize the cannabis material and change the color to purple. While the present invention is described in terms of delta-9 tetrahydrocannabinol, the present invention can also be used in the production of other isomers including delta-8 tetrahydrocannabinol having a purple color. The present invention further includes products manufactured with the processes and methods of the present invention.

The WFE maintains sufficient heat and in-situ time to decarboxylate any residual THCA into THC to yield a concentrated THC product, which can be used in orally deliverable products such as edibles, oils, and candies or gummies. The THC product can also be formulated into a vapor oil product that maintains a purple color during its shelf life.

Figure 4:
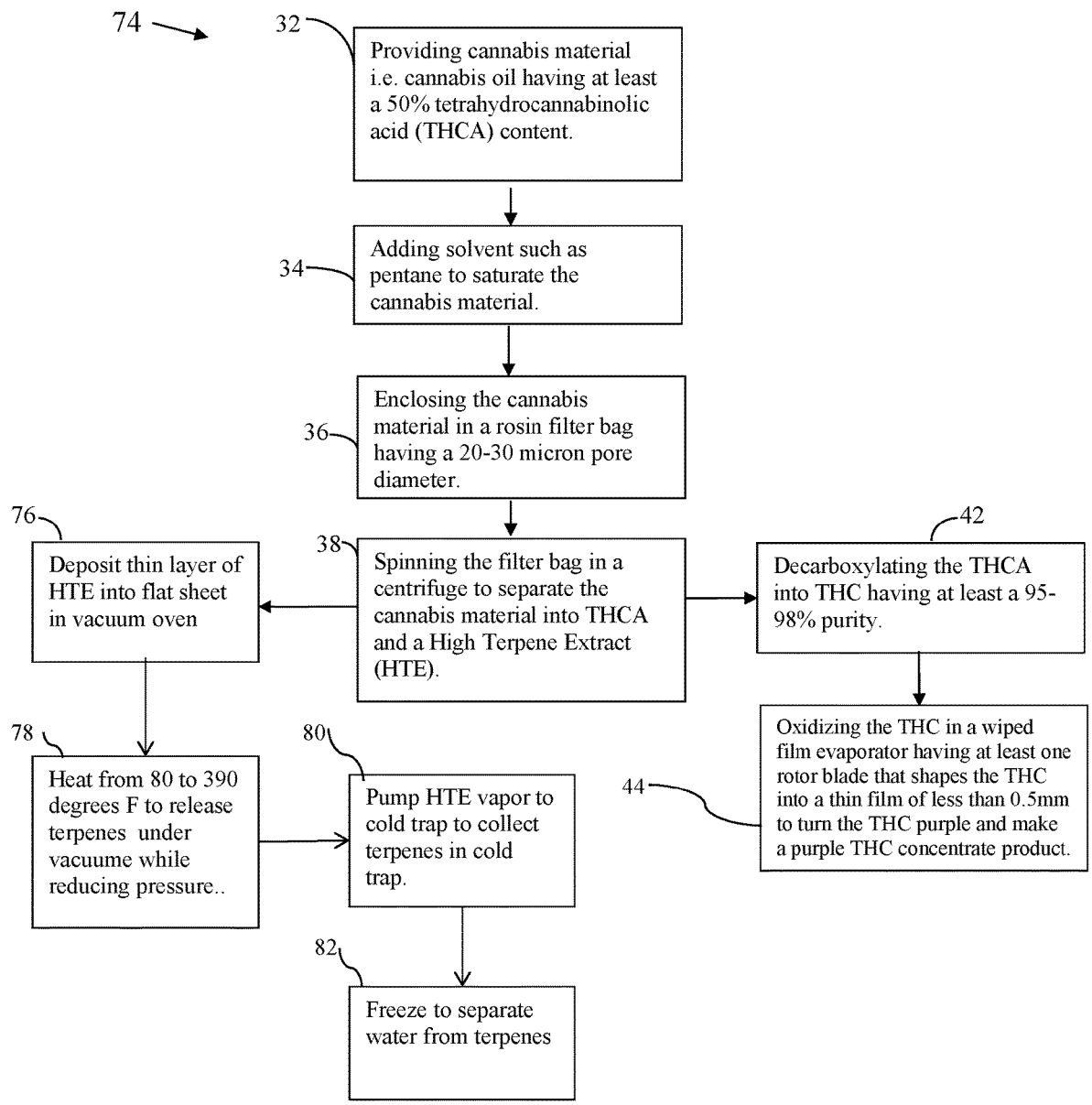
FIG. 4 is a flow chart showing a method of purifying terpenes in a post process using a cold trap.

FIG. 4 shows a method generally designated with the reference numeral 74. The method 74 utilizes a post process to purify cannabis terpenes after the step 38 of spinning a filter bag in a centrifuge to separate cannabis material into THCA and a High Terpene Extract (HTE).

In alternate embodiments, the centrifuge spins, instead of a filter bag, a stainless steel filter basket having a cup, cylinder, or bowl shape. In other embodiments, the centrifuge is adapted to handle filter bags made of sintered metal fiber felt. In further embodiments, the centrifuge is adapted to deliver materials via sintered wire mesh, porous mesh filters, or sintered mesh filters.

After the step 38, the HTE is deposited in a thin layer on a flat tray or sheet capable of insertion into a vacuum oven in step 76. The oven is then pressure sealed. The thin layer is initially less than 1 cm-3 cm in thickness in one embodiment, and preferably less than 0.5 cm in depth in another embodiment. It can be appreciated that there are a number of effective ways to separate water clear terpenes, from a high terpene extract, and leaving any residual cannabinoids such as THC, CBD, THCa or CBDa.

It is possible to distill the high terpene extract in step 76, however, this would require heat which would disrupt the terpene ratios, making them different than the terpene ratios in the original cannabis material. It is also possible to use a rotary evaporator setup to separate terpenes from the high terpene extract, but the rotary evaporator setup is cumbersome and pressures can change rapidly when emptied.

The sheet can be manufactured from borosilicate glass, other high temperature glass, or other suitable non-reactive material. Thicker material may require more time to separate terpenes the high terpene extract. Maximizing pressure reduction optimizes separation and while increasing heat also optimizes separation. For the present invention, it is preferable to reduce heat so as to not tranform any of the terpenes or ratios of terpenes in the terpene mix. Ideally, the lowest pressures and temperatures (approaching ambient, and cooler) is optimal. Practically the temperature range below that which can boil or vaporize THC and CBD, which is 314° F. and 320° F. at 1 ATM pressure.

An example of vacuum ovens utilized in accord with the present invention, can operate at a temperature of +9 degrees F. above ambient to 150° F. above ambient, so a low temperature at near ambient can be achieved, i.e. within 10° F. of ambient temperature of 70° F., or 80° F. The vacuum range potential is 101 kPa. The pressure gauge is rated from 0.0~-101.3 kPa and set pressure ranges are from 5.0~-101.3 kPa. Thus the maximum vacuum utilized is 5 kPa or approximately 0.0493 ATM in one embodiment of the invention. The present invention best preserves the terpene ratios to reflect the cannabis material input by using low pressure and as little heat as possible. Reducing the pressures continuously in a vacuum purge oven (vacuum oven) from 1 ATM to 0.05 ATM and below is feasible. In one embodiment, the operating pressures through the vacuum oven and the cold trap are maintained between 1 ATM and 0.0987 ATM.

The vacuum oven reduces pressure to less than 0.2 ATM to induce volatilization of the at least some of the terpenes in the high terpene extract. Simultaneously the temperature of the vacuum oven is slowly raised from 80 to 390° F. in the step 78. 220 degrees at what vacuum at full vac. to separate terpenes from cannabinoids. During the process of heating, which can take one hour to three hours, the volatile terpenes are nearly 100% in gaseous form.

Below vaporization temp and pressure for cannabinoids these terpenes are pumped in step 80 via an in-line pump or other type of pump into a cold trap to collect terpenes that condense. The step 82 freezes the terpenes to separate water ice. The step of freezing can be between −80° C. to −50° C. in various embodiments of the invention because most terpenes have a relatively low freezing point. Adjustment of the freezing point can selectively remove terpenes. Freezing temperatures can be adjusted over time to reach 0° C. to selectively remove terpenes over time at particular temperatures. In one embodiment the temperatures are pre-programmed at desired intervals.

The cold trap is preferably a vacuum cold trap having a capability to reach temperatures of −50° C. to rapidly chill a flow of terpenes and enable removal of water. A cold trap having a refrigerated vacuum container in fluid communication with an inlet device, a vacuum pump and an outlet device. The cold trap received volumes of purified terpenes via the inlet device in accord with the present invention. It can be set up to sit beside the vacuum oven to enable vacuum pressure to continuously be applied to fluid within the system, such as the high terpene extract in accordance with the present invention. The outlet delivers purified terpene mixture with little, if any water.

Terpenes purified in accordance with the present invention include all of the terpenes found in *Cannabis Sativa* L., including myrcene, pinene, limonene, linalool, humulene, caryophyllene, ocimene, terpinolene, terpineol, geraniol, borneol, bisabolol, camphene, eucalyptol, nerolidol, guaiol, and delta 3 carene. It can be appreciated that most of these terpenes can also be found in various plants other than *Cannabis Sativa* L. Accordingly, the processes of the present invention relying on a high terpene extract, can be applied regardless of the source of the terpenes, including plants that are unrelated to *Cannabis Sativa* L.

Importantly, the present invention separates cannabis material into various chemical components using the minimum amount of heat possible to firstly preserve acidic forms of cannabinoids, to enable cold separation of crystallized THCA, for example. Similarly, the cannabis terpenes are handled and processed with minimal heat, and although they typically don't crystallize, they do condense at particular pressures and can be separated without excessive heat. Excessive heat would be sufficient to volatilize or boil cannabinoids that are residual in the high terpene extract. In this way there is zero, or nearly zero percent cannabinoid content in the extracted terpenes on a weight to weight basis. Normally there is no detectable cannabinoids, as mentioned herein, in the purified terpenes yielded by the process of FIG. 4.

I claim:

1. A method for purifying terpenes, comprising:
   providing cannabis material having a detectable tetrahydrocannabinolic acid (THCA) content;
   adding a solvent to the cannabis material;
   enclosing the cannabis material in a filter bag, the filter bag having a pore diameter of between 20-30 microns;
   spinning the filter bag in a centrifuge to separate the cannabis material into tetrahydrocannabinolic acid (THCA) and a high terpene extract (HTE);

depositing the high terpene extract on a tray;
heating the high terpene extract in a vacuum oven, and reducing pressure within the vacuum oven to volatilize most of the terpenes in the high terpene extract;
pumping the volatilized terpenes from the vacuum oven to a cold trap and condensing the volatilized terpenes in the cold trap to yield condensed terpenes, and
cooling the condensed terpenes at a temperature between −50° C. and 0° C. to remove water from the condensed terpenes to yield purified terpenes.

2. The method of claim 1, wherein the cannabis material has a terpene profile, and the purified terpenes have the same terpene profile as the cannabis material on a relative basis.

3. The method of claim 1, wherein the HTE is deposited in a thin layer of no more than 1 cm on a flat tray or sheet capable of insertion into a vacuum oven, next the vacuum oven is then pressure sealed.

4. The method of claim 3, wherein the thin later is less than 0.5 cm thick.

5. The method of claim 1, wherein the purified terpenes are selected from the group consisting of: myrcene, pinene, limonene, linalool, humulene, caryophyllene, ocimene, terpinolene, terpineol, geraniol, borneol, bisabolol, camphene, eucalyptol, nerolidol, guaiol, and delta 3 carene.

6. The method of claim 1, wherein the purified terpenes are selected from the group consisting essentially of: myrcene, pinene, limonene, linalool, humulene, caryophyllene, ocimene, terpinolene, terpineol, geraniol, borneol, bisabolol, camphene, eucalyptol, nerolidol, guaiol, and delta 3 carene.

7. A method for purifying terpenes, comprising:
providing cannabis material having a detectable tetrahydrocannabinolic acid (THCA) content;
adding a solvent to the cannabis material;
enclosing the cannabis material in a stainless steel filter basket having a pore diameter of between 20-30 microns;
spinning the filter basket in a centrifuge to separate the cannabis material into tetrahydrocannabinolic acid (THCA) and a high terpene extract (HTE) containing terpenes;
decarboxilating at least a portion of the tetrahydrocannabinolic acid into tetrahydrocannabinol (THC);
delivering the high terpene extract into a vacuum oven and reducing pressure to volatilize most of the terpenes in the high terpene extract;
pumping the volatilized terpenes from the vacuum oven and condensing the volatilized terpenes in a cold trap to yield condensed terpenes;
cooling the condensed terpenes at a temperature between −50° C. and 0° C. to remove water from the condensed terpenes to yield purified terpenes;
combining at least a portion of the purified terpenes with the tetrahydrocannabinol in an edible food product.

8. The method as set forth in claim 7, wherein the cannabis material has a terpene profile, and the condensed terpenes mimic the terpene profile of the cannabis material so that the edible food product that smells like the cannabis material.

9. The method as set forth in claim 7, wherein the cannabis material has a terpene profile, and the condensed terpenes mimic the terpene profile of the cannabis material so that the edible food product provides is capable of providing an entourage effect to a user.

10. The method as set forth in claim 7, wherein the tetrahydrocannabinol has visible purple crystals.

11. The method as set forth in claim 7, wherein the tetrahydrocannabinol has visible purple crystals that coat a portion of the food product.

12. The method as set forth in claim 7, wherein the tetrahydrocannabinol has purple crystals that are embedded in the food product.

13. The method as set forth in claim 7, wherein the tetrahydrocannabinol and the purified terpenes are mixed prior to combining the tetrahydrocannabinol and the purified terpenes into the food product.

14. The method as set forth in claim 7, wherein the tetrahydrocannabinol and the purified terpenes are not mixed prior to combining the tetrahydrocannabinol and the purified terpenes into the food product.

15. The method as set forth in claim 7, wherein the food product is cooked prior to the combining of tetrahydrocannabinol and the purified terpenes into the food product so that the terpenes and the tetrahydrocannabinol are not exposed to excessive heat.

16. The method as set forth in claim 7, wherein the food product is pasteurized prior to the combining of tetrahydrocannabinol and the purified terpenes into the food product so that the terpenes and the tetrahydrocannabinol are not exposed to excessive heat.

17. A method for purifying terpenes, comprising:
providing cannabis material having a detectable tetrahydrocannabinolic acid (THCA) content;
adding a solvent to the cannabis material;
enclosing the cannabis material in a stainless steel filter basket having a pore diameter of between 20-30 microns;
spinning the filter basket in a centrifuge to separate the cannabis material into tetrahydrocannabinolic acid (THCA) and a high terpene extract (HTE) containing terpenes;
delivering the high terpene extract into a vacuum oven and reducing pressure to volatilize most of the terpenes in the high terpene extract;
pumping the volatilized terpenes from the vacuum oven and condensing the volatilized terpenes in a cold trap to yield condensed terpenes;
cooling the condensed terpenes at a temperature between −50° C. and 0° C. to remove water from the condensed terpenes to yield purified terpenes;
providing an edible food product;
combining the tetrahydrocannabinolic acid in the edible food product;
cooking the edible food product to decarboxylate the tetrahydrocannabinolic acid into tetrahydrocannabinol; and
adding at least a portion of the purified terpenes to the edible food product after it is cooked.

18. The method as set forth in claim 17, wherein the THCA is at least partially decarboxylated prior to the step of cooking.

19. The method as set forth in claim 17, wherein the tetrahydrocannabinol forms purple crystals that are visible, and the purple crystals are combined with the edible food product.

20. The method as set forth in claim 17, wherein the tetrahydrocannabinol forms purple crystals that are visible in the edible food product after it is cooked.

* * * * *